US011183277B2

(12) United States Patent
Eiden et al.

(10) Patent No.: US 11,183,277 B2
(45) Date of Patent: Nov. 23, 2021

(54) SECURE ELECTRONIC INFORMATION SYSTEM, METHOD AND APPARATUS FOR ASSOCIATIVE DATA PROCESSING

(71) Applicant: OptumInsight, Inc., Eden Prairie, MN (US)

(72) Inventors: Glen P. Eiden, Forest Lake, MN (US); John L. Wilson, Minneapolis, MN (US); Kristy B. Drollinger, Bloomington, MN (US); M. Evan Hetu, Fresno, CA (US); Kristen C. Edsall, Minneapolis, MN (US); Eric J. Eiden, Stacy, MN (US); Colleen Thilgen, Oakland, CA (US); Daniel M. Diman, Columbus, OH (US)

(73) Assignee: OptumInsight, Inc., Eden Prairie, MN (US)

(*) Notice: Subject to any disclaimer, the term of this patent is extended or adjusted under 35 U.S.C. 154(b) by 875 days.

(21) Appl. No.: 15/717,302

(22) Filed: Sep. 27, 2017

(65) Prior Publication Data
US 2018/0018431 A1    Jan. 18, 2018

Related U.S. Application Data

(63) Continuation of application No. 13/743,982, filed on Jan. 17, 2013, now abandoned.

(60) Provisional application No. 61/587,514, filed on Jan. 17, 2012.

(51) Int. Cl.
*G16H 10/60*     (2018.01)
*G16Z 99/00*     (2019.01)

(52) U.S. Cl.
CPC ............. *G16H 10/60* (2018.01); *G16Z 99/00* (2019.02)

(58) Field of Classification Search
CPC .................................................. G06Q 50/22–24
See application file for complete search history.

(56) References Cited

U.S. PATENT DOCUMENTS

| | | | | |
|---|---|---|---|---|
| 2003/0225597 A1* | 12/2003 | Levine | ................... | G16H 50/20 705/3 |
| 2004/0189718 A1* | 9/2004 | Stein | ...................... | G16H 10/60 715/853 |
| 2008/0126134 A1* | 5/2008 | Jones | ...................... | G16H 40/20 705/3 |
| 2008/0183508 A1* | 7/2008 | Harker | ................... | G16H 10/60 705/4 |
| 2009/0136111 A1* | 5/2009 | Jabri | ...................... | G16H 15/00 382/132 |
| 2009/0254376 A1* | 10/2009 | Martinez | ................ | G06Q 10/00 705/3 |
| 2009/0271218 A1* | 10/2009 | Mok | ...................... | G16H 20/00 705/3 |

(Continued)

*Primary Examiner* — Robert A Sorey
(74) *Attorney, Agent, or Firm* — Seyfarth Shaw LLP; Brian Michaelis

(57) ABSTRACT

Intelligence and analytics may be improved by combining sets of disparate data records and matching records between entities. The matched records may then be analyzed by identifying relevant entities and providing information to a user containing the combined sets of secure data records and the analysis. The information may be customized for the user after identifying the user accessing the interface. Additionally, rules may be applied to the analyzed data to enhance the data when viewed by the user.

13 Claims, 14 Drawing Sheets

(56) References Cited

U.S. PATENT DOCUMENTS

| | | | | |
|---|---|---|---|---|
| 2011/0301977 A1* | 12/2011 | Belcher | G16H 10/60 | 705/3 |
| 2011/0301982 A1* | 12/2011 | Green, Jr. | G16H 50/20 | 705/3 |
| 2012/0166462 A1* | 6/2012 | Pathak | G06F 3/04845 | 707/758 |
| 2013/0191157 A1* | 7/2013 | Eiden | G06F 19/00 | 705/3 |
| 2013/0197936 A1* | 8/2013 | Willich | G06Q 50/22 | 705/3 |
| 2015/0193588 A1* | 7/2015 | Nemoto | G06F 19/00 | 705/2 |

* cited by examiner

Sanchez, Emily  (18031891)

DOB: 06/13/1999
Gender: Female
Preferred Language: English
Risk Score: 1.3

Payer: BCBS
Attributed Provider: Johnson, Thomas MD (Pediatrics)
Last Appointment: 01/12/2012 (ED Visit Follow-up)
Next Appointment: None Scheduled ★ High Risk
♦ High Impact

Problem List  ☑ View Resolved

| Date Added | Description | Status |
|---|---|---|
| 07/11/2007 | Asthma | Chronic |
| 03/23 | | |
| 01/05 | | |

- Family History
- Allergies: Aspirin, Penicillin

This is the patient summary: combines clinical, claims, survey data for a more complete patient history (longitudinal view). Alerted to issues, such as the unfilled prescription below

Medication List

| Prescribed | Medication | Indication | Last Filled |
|---|---|---|---|
| 02/12/2012 | Azmacort | Asthma | Unfilled |
| 01/28/2009 | Prednisone | Asthma | 01/29/2012 |
| 07/11/2007 | Proventil HFA | Asthma | 01/20/2012 |

Key Clinical Values

| Date | Type | Result | Expected Range |
|---|---|---|---|
| Vital Signs | | | |
| 02/12/2012 | Weight | 110 lbs. | 80 - 110 lbs. |
| 02/12/2012 | BP | 116 / 68 | < 120 / 80 |
| Disease Specific Values | | | |

Pre-Visit Planning  [View Summary]

Appointment Date: 02/13/2012
Provider: Johnson, T. MD (Pediatrics)

- ☐ Medication Review
- ☐ ER Utilization Assessment
- ☐ Administer PHQ2
- ☐ Asthma Follow-Up Assessment
- ☐ Schedule Appointment  [5]

[Contact Patient]  [Schedule Appt.]

Planning Contact History

| Date | Method | Outcome | Comments |
|---|---|---|---|
| 02/13/2012 | Call | Successful | |
| 02/13/2012 | Call | Left Voicemail | f/u In An hour |

Scroll down

⊘OPTUM  Home  My Patients  Opportunities  Benchmarking

Mon February 13 Patient Dashboard

Filter

Patients

△ Provider    Reset

☑ Harrison, William MD
☑ Hayes, Rutherford PA
☑ Lucy Hayes, MD
☑ Lane, Harriet DO
☑ Thomas Johnson, MD △ Reason For Contact    Reset ☑ ED Follow-Up
☑ Inpatient Follow-Up
☑ Pre-Visit Planning
☑ Proactive Outreach
☑ Visit Follow-Up △ Status    Reset ☑ New
☑ Second Attempt
☑ Third Attempt
☑ Scheduled Follow-Up

| ☐ Patient | ☐ Provider | ☐ Reason For Contact | ☐ Status | ☐ Details | ☐ Contact Priority |
|---|---|---|---|---|---|
| Sanchez, Emily | Johnson, Thomas MD | ED Follow-Up | New | Pre-Visit planning/schedule visit | 767 |
| Abel, Mark | Harrison, William MD | Pre-Visit Planning | New | Upcoming appointment 02/15/2012 | 715 |
| Enright, Valerie | Hayes, Rutherford PA | ED Follow-Up | New | Pre-Visit planning/schedule visit | 699 |
| Panagopoulos, George | Hayes, Lucy MD | Pre-Visit Planning | Scheduled Follow-Up | Planning appointment 02/16/2012 | 687 |
| Smith, Janine | Lane, Harriet DO | Pre-Visit Planning | Second Attempt | Planning appointment 02/17/2012 | 645 |
| Singh, Amit | Johnson, Thomas MD | Proactive Outreach | New | Disease monitoring enrollment | 640 |
| Brown, Derek | Hayes, Rutherford PA | Pre-Visit Planning | Second Attempt | Upcoming appointment 02/21/2012 | 571 |
| Hurrell, Shirley | Lane, Harriet DO | Proactive Outreach | Third Attempt | Disease monitoring enrollment | 548 |
| Wellington, Sara | Harrison, William MD | ED Follow-Up | Third Attempt | COPD, exacerbation | 540 |
| Schoenherr, Walter | Lane, Harriet DO | Inpatient Follow-Up | Second Attempt | Upcoming appointment | 537 |

FIG. 10

SECURE ELECTRONIC INFORMATION SYSTEM, METHOD AND APPARATUS FOR ASSOCIATIVE DATA PROCESSING

CROSS REFERENCE TO RELATED APPLICATIONS

This application is a continuation of U.S. patent application Ser. No. 13/743,982 filed Jan. 17, 2013 which claims the benefit of U.S. Provisional Application No. 61/587,514 filed Jan. 17, 2012, both of which are hereby incorporated by reference in their entirety.

FIELD OF THE INVENTION

This invention relates to apparatuses, systems, and methods for healthcare intelligence and analytics, and more particularly relates to analyzing disparate healthcare data to provide health intelligence to healthcare team members and patients for making better healthcare decisions and systems designed to assist in that care management.

DESCRIPTION OF THE RELATED ART

Decisions regarding the healthcare of an individual are often made by a healthcare team of individuals, physicians, and organizations. In order to make the proper decisions, a healthcare team must rely on a variety healthcare data records, and each of the healthcare data records may include different information. A drawback of providing a variety of disparate healthcare data records to the healthcare team members is that they may not be able to interpret all the disparate data or the ability to display it in one unified way. As a consequence, providing all the healthcare data records directly to the healthcare team members leads to additional administrative expenses to sift through disparate healthcare data records and identify the healthcare data records that each member can interpret. In some instances, the lack of coordinated data can compromise the health and wellbeing of patients.

Conventional patient healthcare systems attempt to solve the problem by providing different healthcare data records to different members of the healthcare team to aid in the decision making. For example, a physician may often rely on only past clinical healthcare data records about a particular patient in making healthcare decisions for the patient. Conversely, healthcare companies may rely on only claims healthcare data records about the patient in providing advice to the patient. In this instance, the health plan and the physician have different data on the patient, which may or may not be coordinated or show the whole picture of the patient's activities.

However, the disconnect between information relied upon and the lack of collaboration when using a conventional patient healthcare system results in sub-optimal healthcare for an individual. Additionally, the healthcare decisions made with the aid of conventional systems must be made on only partial data because only part of the entire list of healthcare data records was made available to each healthcare team member, which further leads to sub-optimal healthcare.

SUMMARY OF THE INVENTION

Apparatuses, systems, and methods for analyzing and displaying disparate secure data may provide intelligence to users of the data and permit better decisions based on the disparate data. Rather than providing separate data to different teams of users from disparate systems, a single system may receive all the disparate data records, process the disparate data records, and present the results in a manner that is easily interpreted and accessed by each member of different team members with access to the secure system through an interface that is accessible to each member. Such a system allows members of a team to make fully-informed decisions based on a variety of disparate data records, and not only a portion of the disparate data records. The system may also provide a platform upon which team members can add additional data on activities they will undertake based on analysis of the disparate data records.

In one implementation, apparatuses, systems, and methods for analyzing and displaying disparate healthcare data may provide health intelligence to healthcare team members and patients, which enables better healthcare decisions. Rather than providing separate data to different members of a healthcare team, a single system may receive all the disparate healthcare data records, process the disparate healthcare data records, and present the results in a manner that is easily interpreted and accessed by each member of a patient's healthcare team through an interface that is accessible to each member. Such a system allows members of a patient's healthcare team to make fully-informed decisions based on a variety of disparate healthcare data records, and not only a portion of the disparate healthcare data records. The system may also provide a platform upon which health care team members can add additional data on activities they are providing to the patient.

Rapidly expanding use of health electronic health record (EHR) and health information exchange (HIE) technology is unlocking rich information on patient clinical experiences that has traditionally been confined to paper records. In a secure environment that protects patient privacy, applications of this apparatus and method of this disclosure marry this data with related health claims, patient-reported outcomes information, and analytics capabilities, and delivers it to the point of care through user-friendly applications. This makes it easier for care team members and patients to access health intelligence that supports better care decisions and patient-centered collaboration. The solutions can also automatically gather performance metrics essential to supporting cost-risk bearing medical organizations, such as Accountable Care Organizations, achieving health-quality objectives and meeting regulatory compliance reporting requirements, which often drive compensation to providers.

The system for analyzing healthcare data disclosed here makes meeting the complex requirements of the health system simple for those expected to make the most important decisions about patient care. It is tailored to the needs of end-users to make it easier for them to access health intelligence for their patients and communities, and to remove the administrative and technological barriers to delivering better, more transparent and more patient-centric health care.

In one embodiment, the system may include a Pathways application for the enrichment of data to augment what is already known about the patients. This application may aid in the development of customized, multi-provider care plans for patients based on patient's individual needs. The system may also include a Care coordination application that provides tools that closely track and document patient care across settings and providers, thus enhancing visibility into diagnoses and treatments and facilitating team-based interventions for patient care. The system may further include a Quality application that organizes and leverages claims, clinical and outcomes data in real-time, providing reporting and analytics to those who need that information. The system may also include a Population application that improves upon existing registries or lists of people with common needs and helps health executives and other stakeholders understand the health of entire populations of patients.

Data accumulated and analyzed from multiple sets of healthcare records from disparate sources may be used to identify and deliver clinically relevant information to the stakeholders of a member's circle of care in a highly relevant, timely, actionable and meaningful way. Data may also displayed through relevant reporting to assist in the administration of the financial aspects of healthcare. This information may describe a member's array of clinical conditions and the factors contributing to the likelihood of poor future outcomes. This information may share gaps in care, clinical alerts and other opportunities that can be addressed by a physician, other providers and patients.

According to an embodiment, a method of providing healthcare intelligence and analytics may include receiving a set of claims healthcare data records, a set of clinical healthcare data records, a set of billing healthcare data records, and a set of patient report outcomes healthcare data records, wherein each set of healthcare data records includes a plurality of healthcare data records. The method may also include matching at least one healthcare data record from each set of healthcare data records to each of a plurality of individuals so that each individual of the plurality of individuals is associated with at least one healthcare data record from at least one set of healthcare data records. The method may further include identifying a healthcare data record from at least one of the sets of healthcare data records that is relevant to a target individual. Additionally, the method may also include analyzing the result of associating each individual of the plurality of individuals with at least one healthcare data record from at least one set of healthcare data records and the result of identifying the health care data record relevant to the target individual. The method may further include outputting information to a user interface display based, in part, on the analysis, and identifying a user accessing the user interface display, wherein the information outputted to the user interface display is unique for the user accessing the user interface display.

According to another embodiment, the method may also include grouping the plurality of individuals into separate population cohorts and identifying the population cohorts to which the target individual is grouped.

In one embodiment, the method may include attributing a clinical condition to the target individual using a predictive model and/or clinically-based rules. In a separate embodiment, the method may further include calculating the historical cost or estimating the predicted cost of treatment for the target individual.

In yet another embodiment, the method may also include identifying a clinical and financial risk associated with the target individual. The method may further include generating a care plan for the target individual. According to another embodiment, the method may include calculating and displaying a confidence level for a healthcare decision made available to the user of the user interface display, wherein the healthcare decision is associated with the target individual.

The foregoing has outlined rather broadly the features and technical advantages of the present disclosure in order that the detailed description of the disclosure that follows may be better understood. Additional features and advantages of the disclosure will be described hereinafter which form the subject of the claims of the disclosure. It should be appreciated by those skilled in the art that the conception and specific embodiment disclosed may be readily utilized as a basis for modifying or designing other structures for carrying out the same purposes of the present disclosure. It should also be realized by those skilled in the art that such equivalent constructions do not depart from the spirit and scope of the disclosure as set forth in the appended claims. The novel features which are believed to be characteristic of the disclosure, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present disclosure.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 8 is an illustration showing a result of an analysis to generate a patient history according to one embodiment of a method for providing health intelligence.

FIG. 9 is an illustration showing a result of an analysis to estimate a cost of treatment according to one embodiment of a method for providing health intelligence.

FIG. 10 is an illustration showing a result of an analysis to create population cohorts according to one embodiment of a method for providing health intelligence.

DETAILED DESCRIPTION

Various features and advantageous details are explained more fully with reference to the non-limiting embodiments that are illustrated in the accompanying drawings and detailed in the following description. Descriptions of well-known starting materials, processing techniques, components, and equipment are omitted so as not to unnecessarily obscure the invention in detail. It should be understood, however, that the detailed description and the specific examples, while indicating embodiments of the invention, are given by way of illustration only, and not by way of limitation. Various substitutions, modifications, additions, and/or rearrangements within the spirit and/or scope of the underlying inventive concept will become apparent to those having ordinary skill in the art from this disclosure.

In the following description, numerous specific details are provided, such as examples of programming, software modules, software applications, user selections, network transactions, database queries, database structures, hardware modules, hardware circuits, hardware chips, etc., to provide a thorough understanding of disclosed embodiments. One of ordinary skill in the art will recognize, however, that embodiments of the invention may be practiced without one or more of the specific details, or with other methods, components, materials, and so forth. In other instances, well-known structures, materials, or operations are not shown or described in detail to avoid obscuring aspects of the invention.

A program may be any predefined interaction with a target population aimed at increasing clinical compliance, patient care or satisfaction, and/or quality health initiatives.

A care opportunity or gap in care may be defined as a clinical action that would typically be beneficial to a patient but has yet been performed. An example of this would be an annual cervical cancer screening which has yet to be performed for a patient would be considered a gap in that patient's care. Closing a 'gap' is performed when a clinician performs a required service for a patient that was previously not performed.

Figure 1:
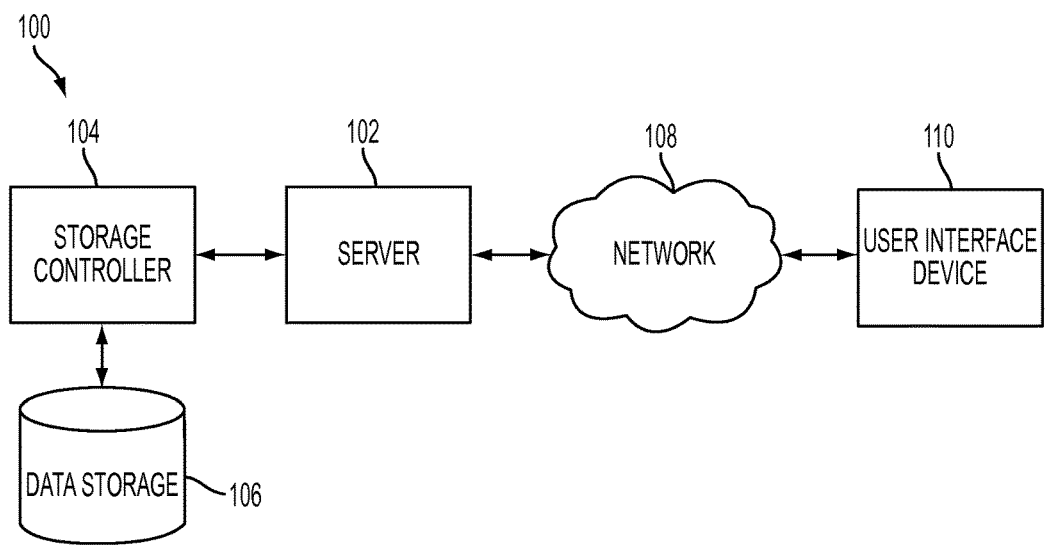
FIG. 1 is a schematic block diagram illustrating one embodiment of a system for providing health intelligence.

FIG. 1 illustrates one embodiment of a system 100 for providing health intelligence. The system 100 may include a server 102, a data storage device 106, a network 108, and a user interface device 110. In a further embodiment, the system 100 may include a storage controller 104, or storage server configured to manage data communications between the data storage device 106, and the server 102 or other components in communication with the network 108. In an alternative embodiment, the storage controller 104 may be coupled to the network 108.

In one embodiment, the system 100 may receive a set of clinical healthcare data records, where the data may include clinical information about an individual, such as medical treatment. The medical treatment may be, for example, prescriptions, instructions from a physician, physical treatments or the like that patient receives from healthcare physicians. The received data may also include a set of claims healthcare data records. According to another embodiment, other healthcare data that the system 100 may receive includes a set of billing healthcare data records. As another example, the healthcare data received may include a set of patient report outcomes healthcare data records.

Each set of healthcare data records may include a plurality of healthcare data records. The system 100 may further match at least one healthcare data record from each set of healthcare data records to each of a plurality of individuals. Each individual of the plurality of individuals may be associated with at least one healthcare data record from at least one set of healthcare data records. Healthcare data records most relevant to a target individual may be identified from the sets of healthcare data records. The system 100 may analyze the results of matching healthcare data records to individuals and identifying healthcare data records relevant to a target individual. The information may be output to a user interface display device 110 through the network 108. The device 110 may display the analysis of the results of matching healthcare data records to individuals and identifying healthcare data records relevant to a target individual. The user interface display device 110 may enable the user to perform analytics, communication, and management. The user accessing the user interface display device 110 may also be identified so that the information output is unique for the user accessing the user interface display device 110.

The user interface display device 110 is referred to broadly and is intended to encompass at least a suitable processor-based device such as a desktop computer, a laptop computer, a Personal Digital Assistant (PDA), a mobile communication device, an organizer device, or the like. In a further embodiment, the user interface display device 110 may access the Internet to access a web application or web service hosted by the server 102 and provide a user interface for enabling a user to enter or receive information. For example, a user may enter clinical and/or non-clinical information about an individual, such as a patient. When the user is a patient, the patient may also enter patient report outcomes data, such responses to questions regarding a particular treatment the patient received.

The system 100 may include a central store of information, such as the storage device 104, that contains patient-centric information that enables analytics and communications (messages, alerts, workflow). The analytics and communications, or messaging, may be timely and updated when new information is available and/or only on a set schedule. The messaging may also be focused and targeted by audience to support attention to those opportunities with the greatest potential to improve health and outcomes.

The network 108 may facilitate communications of data between the server 102 and the user interface device 110. The network 108 may include any type of communications network including, but not limited to, a wireless communication link, a direct PC to PC connection, a local area network (LAN), a wide area network (WAN), a modem to modem connection, the Internet, a combination of the above, or any other communications network now known or later developed within the networking arts which permits two or more computers to communicate with another.

In one embodiment, the server 102 may be configured to receive a set of claims healthcare data records, a set of clinical healthcare data records, a set of billing healthcare data records, and/or a set of patient report outcomes healthcare data records. The server 102 may also be configured to match at least one healthcare data record from each set of healthcare data records to each of a plurality of individuals. Each individual of the plurality of individuals may be associated with at least one healthcare data record from at least one set of healthcare data records. Furthermore, the server 102 may be configured to identify a healthcare data record from at least one of the sets of healthcare data records that is relevant to a target individual. The server 102 may also identify the user accessing the user interface display device 110 and enable the user to perform analytics, communication, and management on the user interface display device 110. The server 102 may access healthcare data records stored in the data storage device 104 via a Storage Area Network (SAN) connection, a LAN, a data bus, a wireless link, or the like.

The data storage device 106 may include a hard disk, including hard disks arranged in a Redundant Array of Independent Disks (RAID) array, a tape storage drive comprising a magnetic tape data storage device, an optical storage device, or the like. In one embodiment, the data storage device 104 may store healthcare related data, such as clinical data, insurance claims data, billing data, patient report outcome data, or the like. The data storage device 104 may also store non-clinical data. The data may be arranged in a database and accessible through Structured Query Language (SQL) queries, or other data base query languages or operations.

The server 102 may execute applications for access data, such as sets of healthcare data records, stored on the data storage device 106. In one embodiment, the server 102 may execute a pathways application, which provides a rich domain specific language (DSL) supporting logic executing in a broad healthcare context, an event processing engine that enables real-time execution of point-of-care clinical decision support, and an intuitive and context sensitive interface that allows business users to author rules and events using natural language construction to describe complex business processes.

The Pathways application may execute logic that takes the previously gathered data and enhance the data available to a user by passing it through various clinical, financial or administrative rules. For example, when a patient is identified as having a simple, but chronic, medical condition, the Pathways application may identify lab data, or other administrative records, that identify the patient as having a potentially more complex version of that condition, thereby enhancing the user's ability to make good clinical choices.

The Pathways application may support the execution of rules and events against multiple forms of source data: provider EMR and billing data, provider cost accounting data, payer claim data sources, administrative data, and third party data sources. Further, Pathways may integrate rules governance, versioning, and content control with the rules and event authoring platform. The Pathways application may be configured to deliver provider analytics and data enrichment that supports reporting and patient care management, to create rules and events that will support care population and care coordination, to develop a set of business logic using a DSL and business object model that is flexible, reusable, to support analysis of provider EMR, lab results, and traditional US professional, facility and pharmacy claims data sources, to process rules execution requests in 'relevant time,' to ensure efficient execution of rules in a scalable architecture that can be used to process large quantities of healthcare data, and to integrate rules governance with rules authoring by linking supporting evidence to measures, assigning review dates, and enabling measure identification with the organization that owns the definition (HEDIS, NQF, etc.).

The server 102 may also execute a Quality application, which allows providers and payers to view reports across clinical and financial dimensions based on data from all healthcare sources and can support flexible, dimensional exploration of measures with the ability to hone in drivers and identify actionable opportunities. The Quality application may leverage cascading metrics that establish clear connections between operational-, program-, and executive-level results. The Quality application may be configured to study performance against shared savings contracts, specifically targeting Medicare shared savings, to understand the drivers underneath shared savings performance (population, cost, and quality), and to use an integration of financial and quality data to drill deeper into performance, to discover opportunities to increase performance and to support the development of programs to increase quality and financial performance.

The server 102 may further execute a Care coordination application. The Care coordination application may improve individual and population health by better informing and attributed providers, care teams and patients about conditions, the available treatments and provider/patient interactions, promote more efficient and effective communication by providing information (analytics-driven out reach, education and care messaging) in an automated, real time manner and integrating it into the provider and consumer workflow, lower medical costs thru timely intervention with patients and healthier populations, establish high performance provider networks and accountable entities by providing actionable information on quality, cost and utilization, and align the efforts above with value-based measurement and incentives/payments to the providers. The Care coordination application may be implemented for patient management, such as adding temporary patients if the patient is not in the client environment and later make them records, providing the ability to add, edit, and search for patients, and adding demographics to the patient record. The Care coordination application may be implemented for work queue management, such as providing the ability for the care manager to view, assign, and prioritize her/his work load, and displaying a care manager's patient workload, alerts, activities, upcoming appointments, and tasks to be completed, completed tasks, and future tasks.

The Care coordination application may be implemented for program, opportunity, and gap determination in care management, such as assigning patients to clinical outreach programs based on analytic and clinician input, discretely tracking patient status within a program across points in time from an initial call, to engagement, to closure, creating care manager opportunities, and reassigning opportunities by the care manager or user. The Care coordination application may also be implemented for tracking outcomes, such as setting goals and activities for patients, ensuring adherence and completion of activities, and viewing activity outcomes. The Care coordination application may further be implemented for assessing patients, such as assessing patient status, acuity, risk, and health management status through discrete answers to predefined questions.

The Care coordination application may further be implemented for presenting clinical data, such as searching for medications, adding medications to a patient record, adding a provider or a facility to a patient record, providing searching for provides or facilities within a patient's network, viewing loinc codes for laboratory and clinical results, providing display imaging, tracking patient biometric information from self-reported data and devices in the patient's home or hospital, and setting up alerts that are displayed when biometric data is abnormal. The Care coordination application may also be implemented for care planning, such as unified presentation of program, opportunity, and gaps in care across a system within a consolidated view, editing the data, and adding patient care notes. The quality application may further be implemented for managing a patient registry, linking to outside tools, reporting data, accepting program nominations from the pathways application, tracking patient engagement, identifying opportunities, tracking outcomes, assessing patients, and planning care.

The Care coordination application may create enhanced data sets that are used by the other applications to display the content. For example, the Pathways application may identify a patient who has a condition. In another example, the Population application may display cohorts of patients who have that condition. The Pathways application may identify the provider who is most likely to be the main provider of care for the patient and display that in many other areas of the application such as reporting and care management. In a display from the Care coordination application the data may display as a primary provider. In other reports, the data may display as the provider who is incentivized for care for that patient.

The server 102 may also execute a Population application, which allows payers and providers to identify population cohorts and risk across clinical and financial dimensions based on data from all healthcare sources as well as deliver analytics (e.g., interactive analytics) that allows actions to be taken automatically or manually. For example, the application may perform categorization of a population into disease registries, and one may perform a stratification of risk within a population. The Population application may be configured to integrate clinical data with claims data, to analyze specific disease risks and registries from that combined data based on the Medicare Shared Savings ACO measures, to provide relatively basic analytics across that data, to allow Care coordination to assign a set of patients from Population to a Care coordination program.

Figure 2:
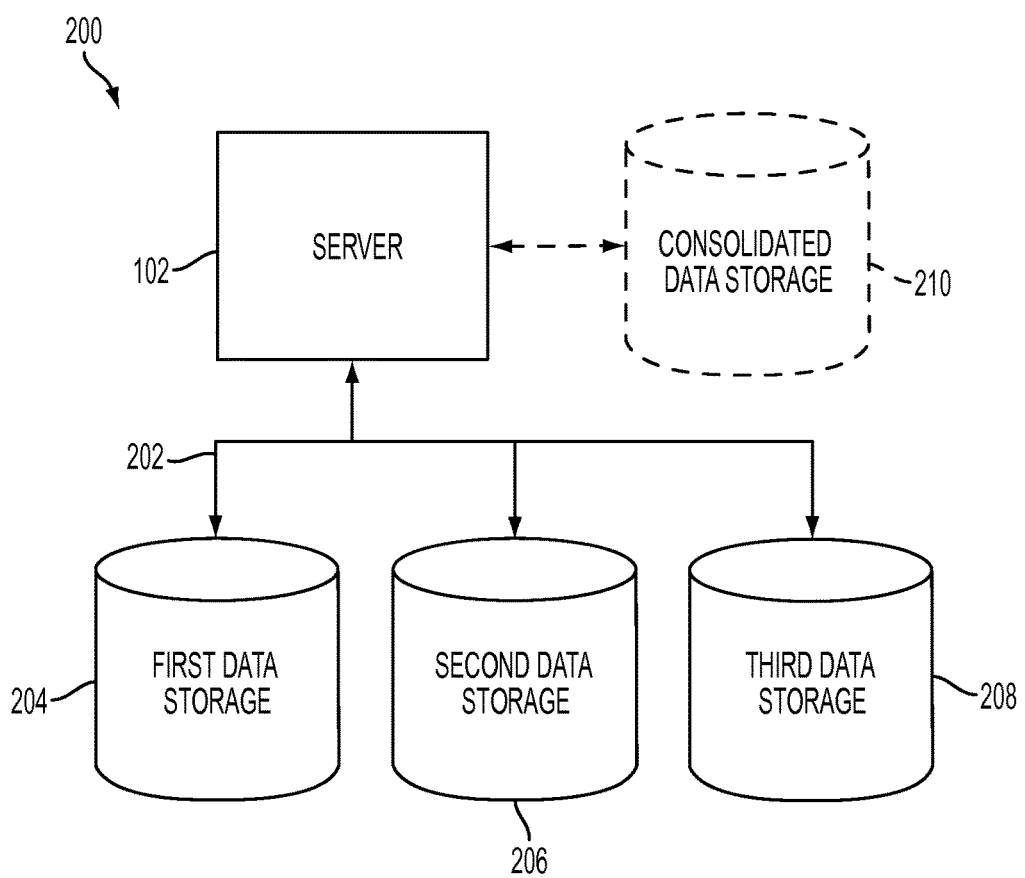
FIG. 2 is a schematic block diagram illustrating one embodiment of a database system for providing health intelligence.

FIG. 2 illustrates one embodiment of a data management system 200 configured to store and manage data for providing healthcare intelligence and analytics. In one embodiment, the system 200 may include a server 102. The server 102 may be coupled to a data-bus 202. In one embodiment, the system 200 may also include a first data storage device 204, a second data storage device 206, and/or a third data storage device 208. In other embodiments, the system 200 may include additional data storage devices (not shown). In such an embodiment, each data storage device 204-208 may host a separate database of a set of healthcare data records and/or programs to execute providing healthcare intelligence and analytics. The storage devices 204208 may be arranged in a RAID configuration for storing redundant copies of the database or databases through either synchronous or asynchronous redundancy updates.

In one embodiment, the server 102 may submit a query to selected data storage devices 204-208 to collect a consolidated set of data elements associated with a healthcare data records. The server 102 may store the consolidated data set in a consolidated data storage device 210. In such an embodiment, the server 102 may refer back to the consolidated data storage device 210 to obtain a set of healthcare data records associated with a specific patient or a plurality of patients. Alternatively, the server 102 may query each of the data storage devices 204-208 independently or in a distributed query to obtain the set of healthcare data records associated with a specific patient or a plurality of patients. In another alternative embodiment, multiple databases may be stored on a single consolidated data storage device 210.

In various embodiments, the server 102 may communicate with the data storage devices 204-210 over the data bus 202. The data bus 202 may comprise a SAN, a LAN, a wireless connection, or the like. The communication infrastructure may include Ethernet, Fibre-Channel Arbitrated Loop (FC-AL), Small Computer System Interface (SCSI), and/or other similar data communication schemes associated with data storage and communication. For example, the server 102 may communicate indirectly with the data storage devices 204-210 by first communicating with a storage server or the storage controller 104.

In one example of the system 200, the first data storage device 204 may store clinical healthcare data records associated with individuals. The clinical healthcare data may include the type of treatments or procedures being performed, and in what distribution they are being performed. The clinical healthcare data may also indicate who provided the treatment, such as a medical doctor, nurse, dentist, or other healthcare professional. As another example, the clinical healthcare data may include the types and volumes of drugs being dispensed by pharmacists. The clinical healthcare data corresponding to the types of procedures being performed may include extraction, surgery, orthodontia, etc.

The second data storage device 206 may include clinical information about the healthcare providers, such as medical treatment. The medical treatment may be, for example, prescriptions, instructions, physical treatments or the like that the healthcare providers provide to patients. The third data storage device 208 may include a set of billing healthcare data records or a set of patient report outcomes healthcare data records. According to one embodiment, the data stored in the data storage devices 204-208 may also be stored in one data storage device instead of separate data storage devices 204-208.

The server 102 may host a software application configured for providing healthcare intelligence and analytics. The software application may further include modules for interfacing with the data storage devices 204-210, interfacing a network 108, interfacing with a user, and the like. In one embodiment, the server 102 may host an engine, application plug-in, or application programming interface (API). In another embodiment, the server 102 may host a web service or web accessible software application.

Figure 3:
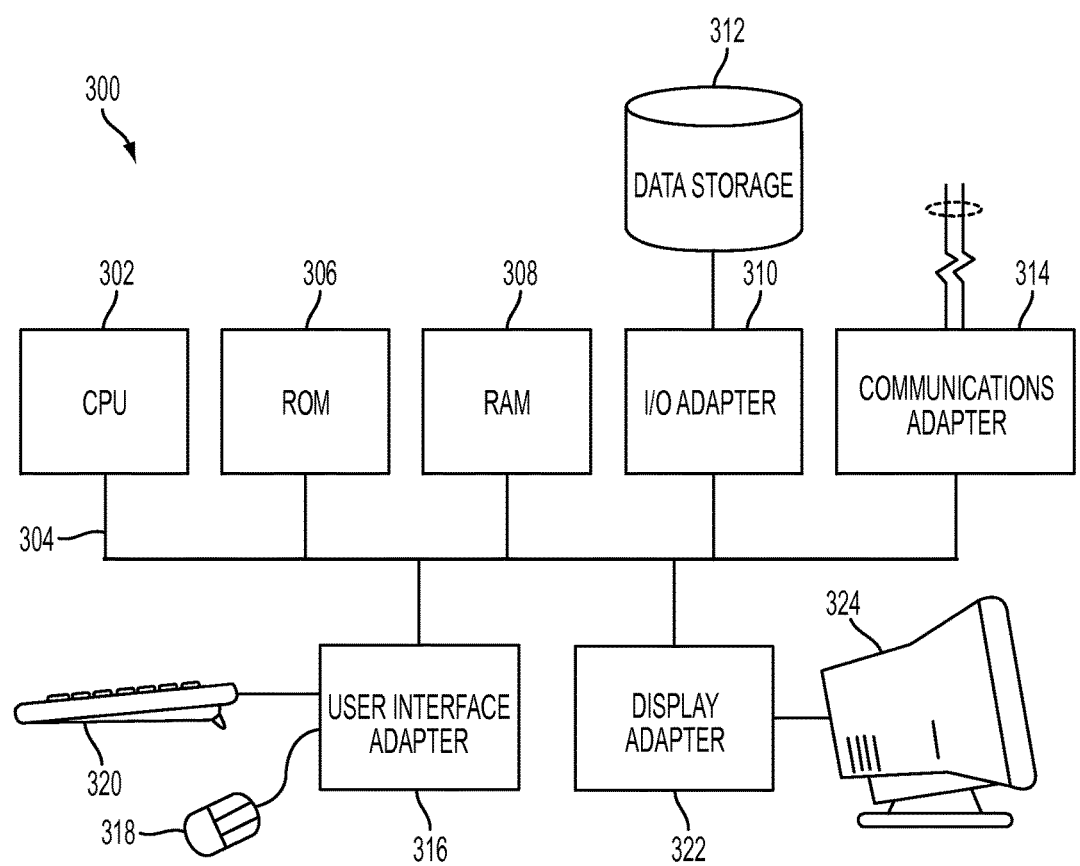
FIG. 3 is a schematic block diagram illustrating one embodiment of a computer system that may be used in accordance with certain embodiments of the system for providing health intelligence.

FIG. 3 illustrates a computer system 300 according to certain embodiments of the server 102 and/or the user interface device 110. The central processing unit (CPU) 302 is coupled to the system bus 304. The CPU 302 may be a general purpose CPU or microprocessor. The present embodiments are not restricted by the architecture of the CPU 302, so long as the CPU 302 supports the modules, applications, and operations as described herein. The CPU 302 may execute various logical instructions according to disclosed embodiments.

The computer system 300 may include Random Access Memory (RAM) 308, which may be SRAM, DRAM, SDRAM, or the like. The computer system 300 may utilize RAM 308 to store the various data structures used by a software application configured for providing healthcare intelligence and analytics. The computer system 300 may also include Read Only Memory (ROM) 306 which may be PROM, EPROM, EEPROM, optical storage, or the like. The ROM may store configuration information for booting the computer system 300. The RAM 308 and the ROM 306 hold user and system 100 data.

The computer system 300 may also include an input/output (I/O) adapter 310, a communications adapter 314, a user interface adapter 316, and a display adapter 322. The I/O adapter 310 and/or user the interface adapter 316 may, in certain embodiments, enable a user to interact with the computer system 300 in order to input information such as patient outcome report data. In a further embodiment, the display adapter 322 may display a graphical user interface associated with a software or web-based application for providing healthcare intelligence and analytics.

The I/O adapter 310 may connect to one or more data storage devices 312, such as one or more of a hard drive, a Compact Disk (CD) drive, a floppy disk drive, a tape drive, to the computer system 300. The communications adapter 314 may be adapted to couple the computer system 300 to the network 108, which may be one or more of a wireless link, a LAN and/or WAN, and/or the Internet. The user interface adapter 316 couples user input devices, such as a keyboard 320 and a pointing device 318, to the computer system 300. The display adapter 322 may be driven by the CPU 302 to control the display on the display device 324.

Disclosed embodiments are not limited to the architecture of system 300. Rather, the computer system 300 is provided as an example of one type of computing device that may be adapted to perform functions of a server 102 and/or the user interface device 110. For example, any suitable processor-based device may be utilized including, without limitation, personal data assistants (PDAs), computer game consoles, and multi-processor servers. Moreover, the present embodiments may be implemented on application specific integrated circuits (ASIC) or very large scale integrated (VLSI) circuits. In fact, persons of ordinary skill in the art may utilize any number of suitable structures capable of executing logical operations according to the disclosed embodiments.

Figure 4:
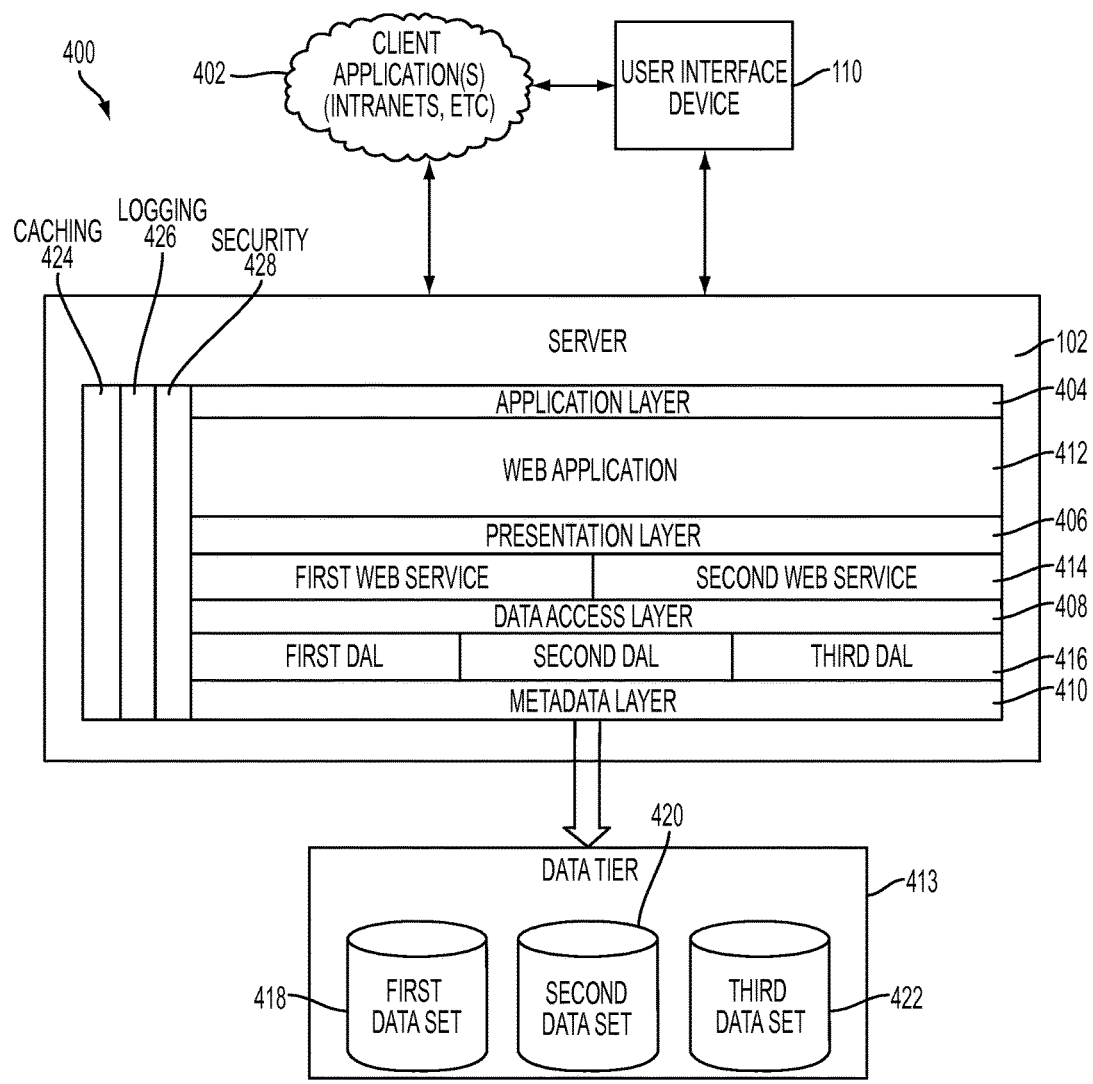
FIG. 4 is a schematic logical diagram illustrating one embodiment of abstraction layers of operation in a system for providing health intelligence.

FIG. 4 illustrates one embodiment of a network-based system 400 for providing healthcare intelligence and analytics. In one embodiment, the network-based system 400 includes a server 102. Additionally, the network-based system 400 may include a user interface device 110. In still a further embodiment, the network-based system 400 may include one or more network-based client applications 402 configured to be operated over a network 108 including a wireless network, an intranet, the Internet, or the like. In still another embodiment, the network-based system 400 may include one or more data storage devices 104.

The network-based system 400 may include components or devices configured to operate in various network layers. For example, the server 102 may include modules configured to work within an application layer 404, a presentation layer 406, a data access layer 408 and a metadata layer 410. In a further embodiment, the server 102 may access one or more data sets 418-422 that comprise a data layer or data tier 413. For example, a first data set 418, a second data set 420, and a third data set 422 may comprise a data tier 413 that is stored on one or more data storage devices 204-208.

One or more web applications 412 may operate in the application layer 404. For example, a user may interact with the web application 412 though one or more I/O interfaces 318, 320 configured to interface with the web application 412 through an I/O adapter 310 that operates on the application layer. In one embodiment, a web application 412 may be provided for providing healthcare intelligence and analytics that includes software modules configured to perform the steps of receiving a plurality of disparate healthcare data records, matching healthcare data records to individuals, identifying healthcare data records relevant to a target individual, analyzing the results of matching healthcare data records to individuals and identifying healthcare data records relevant to a target individual, outputting information to a user interface display device based, in part, on the analysis, and identifying a user accessing the user interface display device.

In a further embodiment, the server 102 may include components, devices, hardware modules, or software modules configured to operate in the presentation layer 406 to support one or more web services 414. For example, a web application 412 may access or provide access to a web service 414 to perform one or more web-based functions for the web application 412. In one embodiment, web application 412 may operate on a first server 102 and access one or more web services 414 hosted on a second server (not shown) during operation.

For example, a web application 412 for providing healthcare intelligence and analytics may access a first web service 414 to receive a set of claims healthcare data records, a set of clinical healthcare data records, a set of billing healthcare data records, and a set of patient report outcomes healthcare data records, wherein each set of healthcare data records may include a plurality of healthcare data records. A second web service 414 may be accessed to match at least one healthcare data record from each set of healthcare data records to each of a plurality of individuals so that each individual of the plurality of individuals is associated with at least one healthcare data record from at least one set of healthcare data records, and to identify a healthcare data record from at least one of the sets of healthcare data records that is relevant to a target individual. In another embodiment, separate web services may be used to analyze the results of matching healthcare data records to individuals and identifying healthcare data records relevant to a target individual, to output information to a user interface display based, in part, on the analysis, and to identify a user accessing the user interface display. One of ordinary skill in the art will recognize various web-based architectures employing web services 414 for modular operation of a web application 412.

In one embodiment, a web application 412 or a web service 414 may access one or more of the data sets 418-422 through the data access layer 408. In certain embodiments, the data access layer 408 may be divided into one or more independent data access layers 416 for accessing individual data sets 418-422 in the data tier 413. These individual data access layers 416 may be referred to as data sockets or adapters. The data access layers 416 may utilize metadata from the metadata layer 410 to provide the web application 412 or the web service 414 with specific access to the data set 412. For example, the data access layer 416 may include operations for performing a query of the data sets 418-422 to retrieve specific information for the web application 412 or the web service 414.

For example, the data access layer 416 may include operations for performing a query of the data sets 418-422 to retrieve specific information for the web application 412 or the web service 414. In a more specific example, the data access layer 416 may include a query for healthcare data records that may include claims, clinical, billing, and patient outcome report data.

Figure 5:
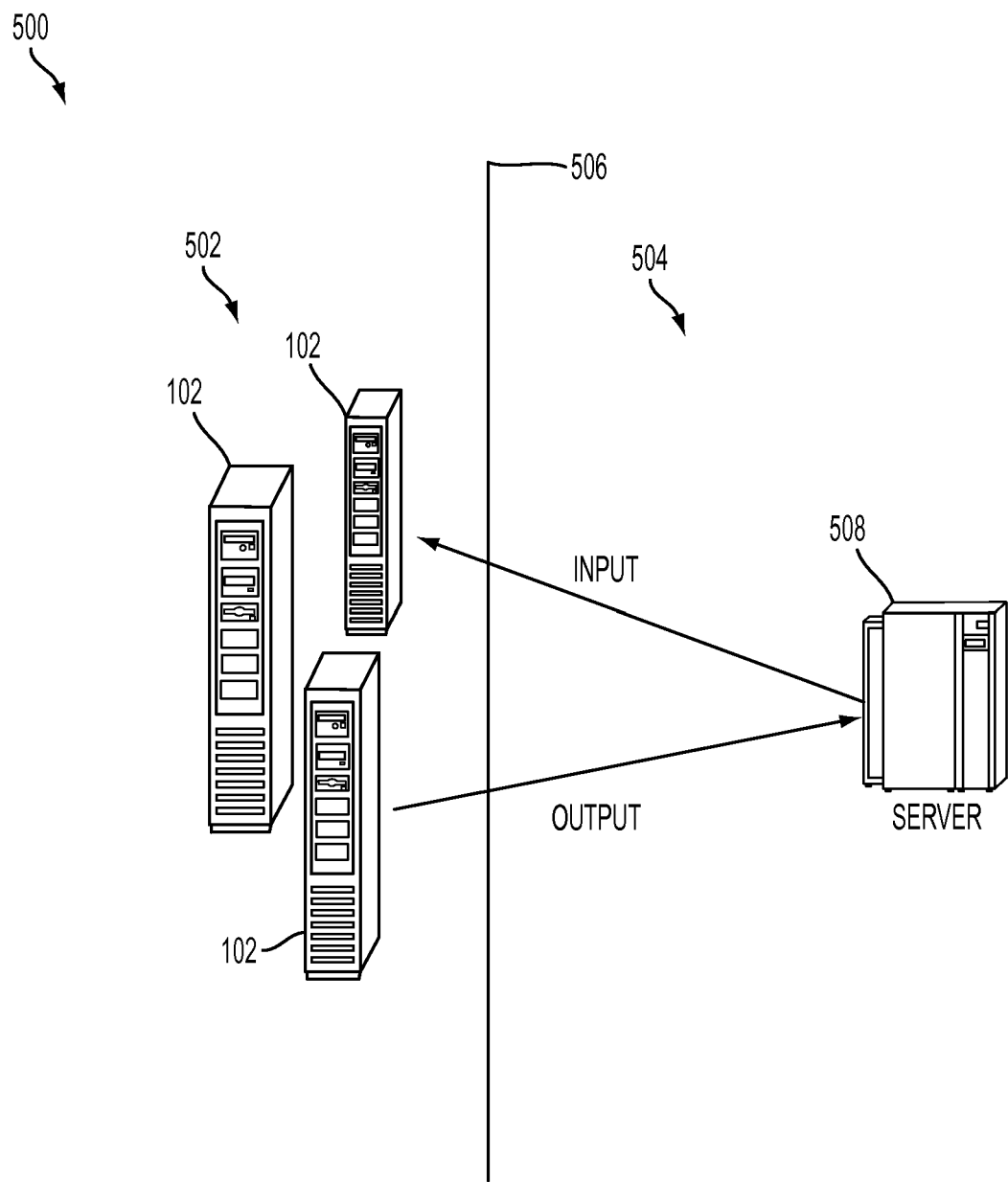
FIG. 5 is a schematic block diagram illustrating one embodiment of a distributed system for providing health intelligence.

FIG. 5 illustrates a further embodiment of a system 500 for providing healthcare intelligence and analytics. In one embodiment, the system 500 may include a service provider site 502 and a client site 504. The service provider site 502 and the client site 504 may be separated by a geographic separation 506.

In one embodiment, the system 500 may include one or more servers 102 configured to host a software application 412 for providing healthcare intelligence and analytics, or one or more web services 414 for performing certain functions associated with providing healthcare intelligence and analytics. The system may further comprise a user interface server 508 configured to host an application or web page configured to allow a user to interact with the web application 412 or web services 414 for providing healthcare intelligence and analytics. In such an embodiment, a service provider may provide hardware 102 and services 414 or applications 412 for use by a client without directly interacting with the client's customers.

Figure 6:
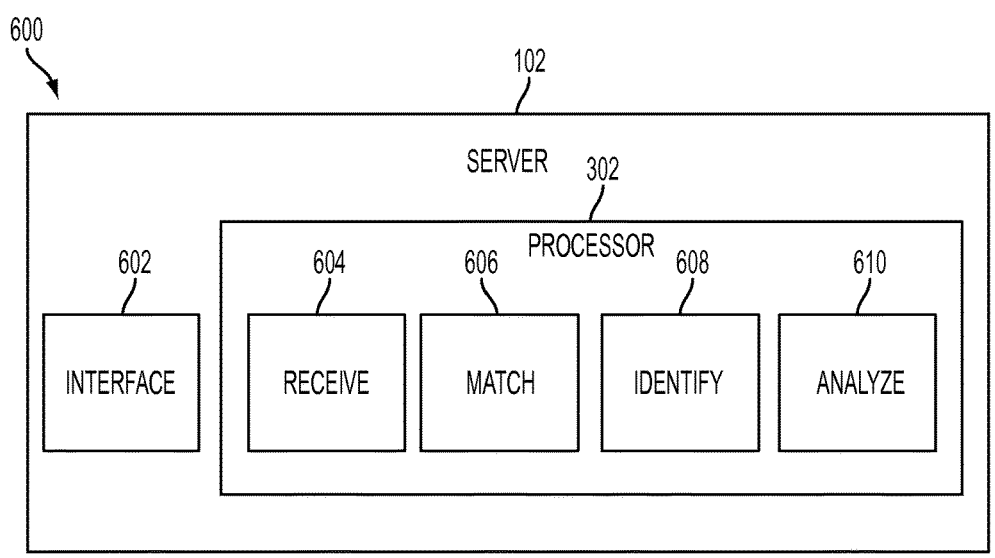
FIG. 6 is a schematic block diagram illustrating one embodiment of an apparatus for providing health intelligence.

FIG. 6 illustrates one embodiment of an apparatus 600 for providing healthcare intelligence and analytics. In one embodiment, the apparatus 600 is a server 102 configured to load and operate software modules 602-610 configured for providing healthcare intelligence and analytics. Alternatively, the apparatus 600 may include hardware modules 602-610 configured with analog or digital logic, firmware executing FPGAs, or the like configured to receive a plurality of disparate healthcare data records, match healthcare data records to individuals, identify healthcare data records relevant to a target individual, analyze the results of matching healthcare data records to individuals and identifying healthcare data records relevant to a target individual, output information to a user interface display device based, in part, on the analysis, and identify a user accessing the user interface display device. In such embodiments, the apparatus 600 may include a processor 302 and an interface 602, such as an I/O adapter 310, a communications adapter 314, a user interface adapter 316, or the like.

In one embodiment, the processor 302 may include one or more software defined modules configured to receive a plurality of disparate healthcare data records, match healthcare data records to individuals, identify healthcare data records relevant to a target individual, analyze the results of matching healthcare data records to individuals and identifying healthcare data records relevant to a target individual, output information to a user interface display device based, in part, on the analysis, and identify a user accessing the user interface display device. In one embodiment, these modules may include an interface module 602 to provide a user with access to the apparatus 600, as well as to output information and identify a user accessing the interface module 602. Other modules may include a receive module 604 to receive a plurality of disparate healthcare data records, a match module 606 to match healthcare data records to individuals, an identify module 608 to identify healthcare data records relevant to a target individual, and an analyze module 610 to analyze the results of matching healthcare data records to individuals and identifying healthcare data records relevant to a target individual.

The sets of healthcare data records received by receive module 604 according to an embodiment of the present disclosure may include claims, clinical, billing, or patient outcome report data. A set of healthcare data records may include clinical information. As one example, healthcare data records may, in certain embodiments, include clinical information about individuals, such as medical treatment. The medical treatment may be, e.g., prescriptions, instructions, physical treatments or the like that patients receive from healthcare physicians.

Although the various functions of the server 102 and the processor 302 are described in the context of modules, the methods, processes, and software described herein are not limited to a modular structure. Rather, some or all of the functions described in relation to the modules of FIG. 6 may be implemented in various formats including, but not limited to, a single set of integrated instructions, commands, code, queries, etc. In one embodiment, the functions may be implemented in database query instructions, including SQL, PLSQL, or the like. Alternatively, the functions may be implemented in software coded in C, C++, C #, php, Java, or the like. In still another embodiment, the functions may be implemented in web based instructions, including HTML, XML, etc.

Generally, the interface module 602 may provide a user with access to the apparatus 600, as well as to output information and identify a user accessing the interface module 602. For example, the interface module 602 may display information related a target patient and allow the user to provide input to manipulate the information displayed via the interface module 602. In a further embodiment, the interface module 602 may display healthcare intelligence and analytics, and allow the user to communicate with other members of an individual's healthcare team or manage the individual's healthcare. For example, healthcare intelligence outputted via the interface module as a result of the analysis performed on the results of matching healthcare data records to individuals and identifying healthcare data records relevant to a target individual may include statistics, tables, charts, graphs, recommendations, and the like.

Structurally, the interface module 602 may include one or more of an I/O adapter 310, a communications adapter 314, a user interface adapter 316, and/or a display adapter 322. The interface module 602 may further include I/O ports, pins, pads, wires, busses, and the like for facilitating communications between the processor 302 and the various adapters and interface components 310-324. The interface module may also include software defined components for interfacing with other software modules on the processor 302.

In one embodiment, the processor 302 may load and execute software modules configured to receive a plurality of disparate healthcare data records, match healthcare data records to individuals, identify healthcare data records relevant to a target individual, analyze the results of matching healthcare data records to individuals and identifying healthcare data records relevant to a target individual, output information to a user interface display device based, in part, on the analysis, and identify a user accessing the user interface display device for providing healthcare intelligence and analytics. These software modules may include a receive module 604 to receive a plurality of disparate sets of healthcare data records, a match module 606 to match healthcare data records to individuals, an identify module 608 to identify healthcare data records relevant to a target individual, and an analyze module 610 to analyze the results of matching healthcare data records to individuals and identifying healthcare data records relevant to a target individual. In one embodiment, the interface module 602 may be used to output information based, in part, on the analysis of the results of matching healthcare data records to individuals and identifying healthcare data records relevant to a target individual, and to identify a user accessing the user interface display device.

In a specific embodiment, the processor 302 may load and execute computer software configured to receive a set of claims healthcare data records, a set of clinical healthcare data records, a set of billing healthcare data records, and a set of patient report outcomes healthcare data records. For example, the receive module 604 may receive, from a plurality of healthcare data sources, the set of claims healthcare data records, the set of clinical healthcare data records, the set of billing healthcare data records, and the set of patient report outcomes healthcare data records. The set of clinical healthcare data records may include, for example, the type of procedures or medical treatments being performed on individuals or it may include the types and volumes of drugs being dispensed by pharmacists to the individual. The medical treatment may be, e.g., prescriptions, instructions, physical treatments or the like that the healthcare providers provide to patients. The set of claims healthcare data records may include, for example, dates of medical services, payment amounts for services, procedure and diagnostic codes, and/or various identification numbers for patient, provider and facility. The set of billing healthcare data records may include, for example, information about the encounter with the provider, such as place of service, billing amounts, and/or payment amounts for those services. The set of patient reported outcomes healthcare data records may include, for example, pre- and post-service quality of life, range of motion for joint issues, and/or general health perceptions from the patient's viewpoint.

The match module 606 may, in one embodiment, be configured to match at least one healthcare data record from each set of healthcare data records to each of a plurality of individuals so that each individual of the plurality of individuals is associated with at least one healthcare data record from at least one set of healthcare data records. According to yet another embodiment, the identify module 608 may be configured to identify a healthcare data record from at least one of the sets of healthcare data records that is relevant to a target individual.

Figure 9:
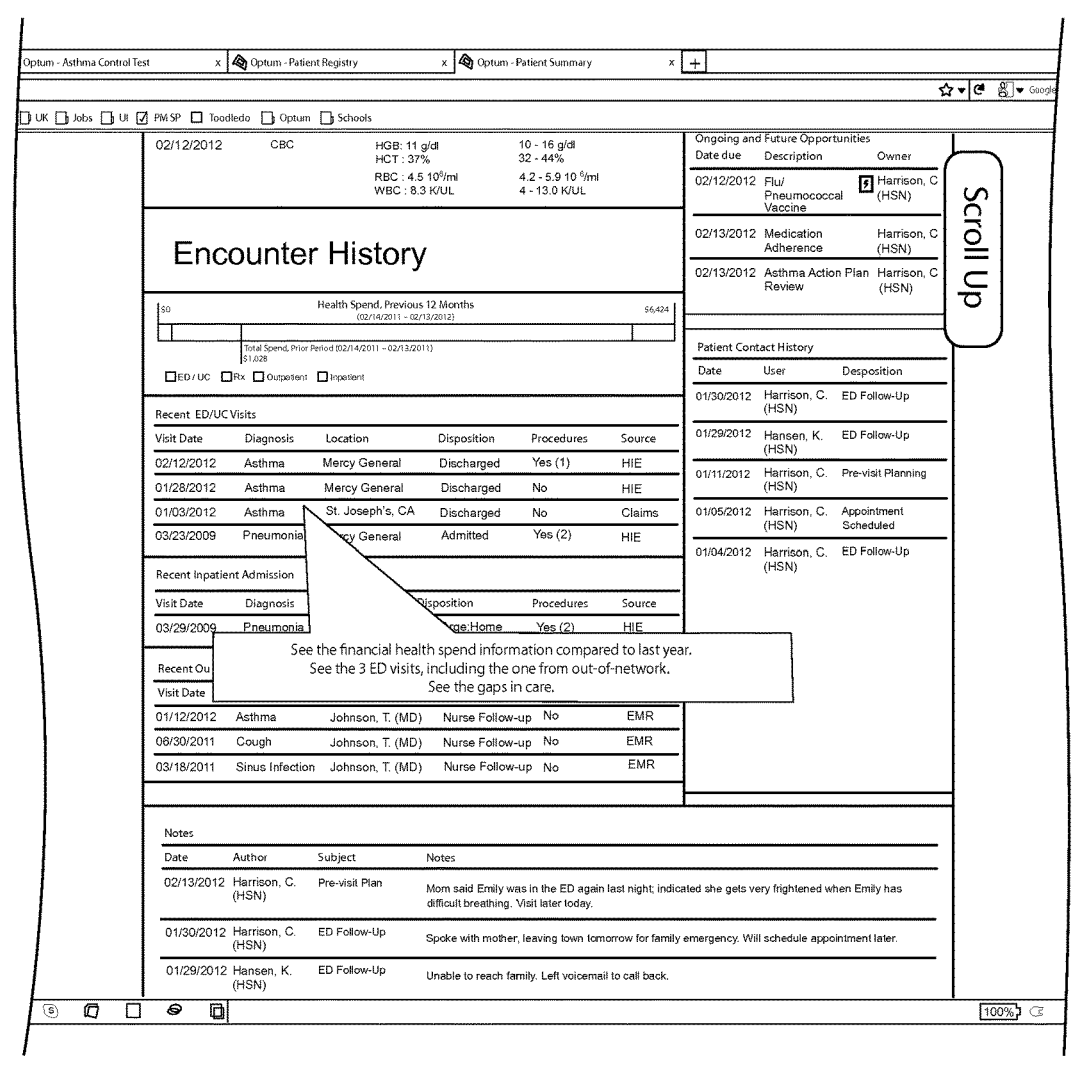

The analyze module 610 may, according to an embodiment, analyze the result of associating each individual of the plurality of individuals with at least one healthcare data record from at least one set of healthcare data records and the result of identifying the health care data record relevant to the target individual. For example, as shown in FIG. 8, analyzing may result in the generation of a complete patient history. In one embodiment, the analyze module 610 may include grouping the plurality of individuals into separate population cohorts and identifying the population cohorts to which the target individual is grouped, as shown in FIG. 10. In another embodiment, the analyze module 610 may include attributing a clinical condition to the target individual using a predictive model, while in another embodiment, the analyze module 610 may include estimating a cost of treatment for the target individual, as shown in FIG. 9. According to one embodiment, the analyze module 610 may further include identifying a clinical and financial risk associated with the target individual or generating a care plan for the target individual. In yet another embodiment, the analyze module 610 may include calculating and displaying a confidence level for a healthcare decision made available to the user of the user interface display, wherein the healthcare decision is associated with the target individual.

Figure 7:
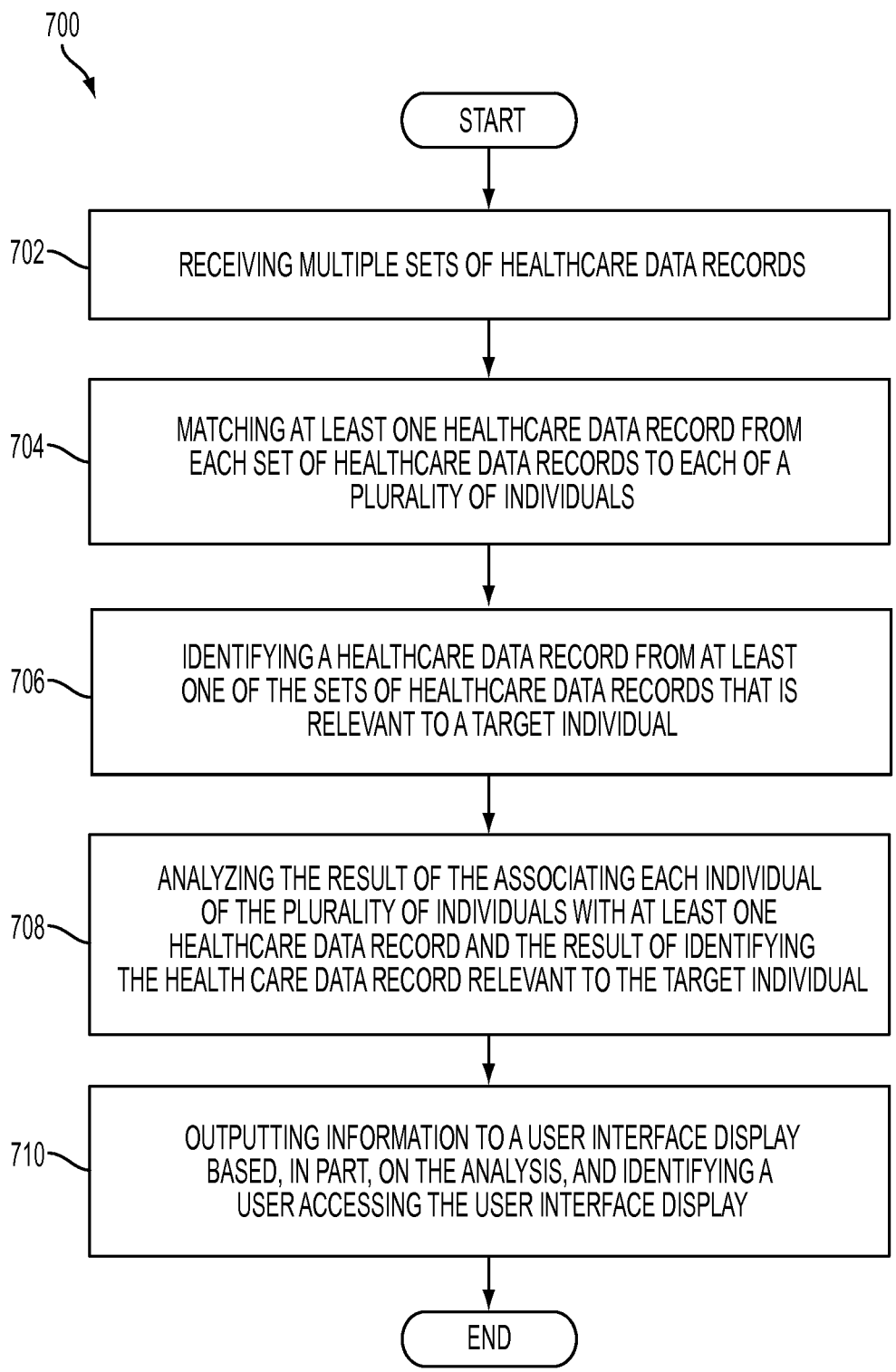
FIG. 7 is a flow chart illustrating one embodiment of a method for providing health intelligence.
Figure 12:
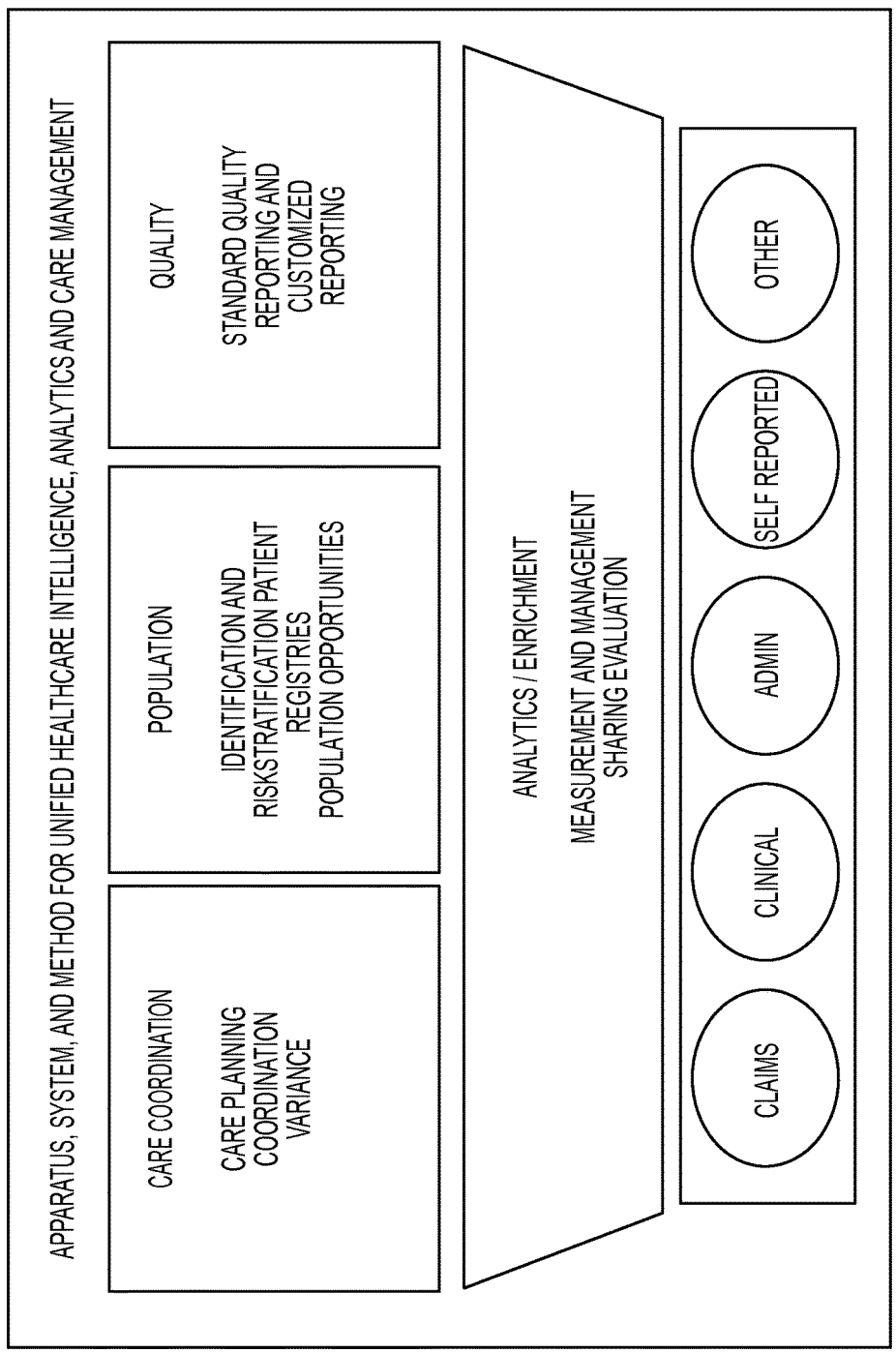
FIG. 12 is an illustration showing a system diagram including data inputs and segmentation of functionality across the system according to one embodiment of the disclosure.

FIG. 7 illustrates one embodiment of a method 700 for providing health intelligence. In one embodiment, the method 700 starts at block 702 with receiving multiple sets of healthcare data records. In one embodiment, the multiple sets of healthcare data records may include claims, clinical, admin, billing, patient reported outcome healthcare data records, and/or other data records for a plurality of individuals. FIG. 12 is an illustration showing a system diagram including data inputs and segmentation of functionality across the system according to one embodiment of the disclosure.

At block 704, the method 700 may include matching at least one healthcare data record from each set of healthcare data records to each of a plurality of individuals. Each individual of the plurality of individuals may be associated with at least one healthcare data record from at least one set of healthcare data records.

The method 700 may further include, at block 706, identifying a healthcare data record from at least one of the sets of healthcare data records that is relevant to a target individual. In one embodiment, the method 700 may further include, at block 708, analyzing the result of associating each individual of the plurality of individuals with at least one healthcare data record and the result of identifying the health care data record relevant to the target individual.

For example, as shown in FIG. 8, analyzing may result in the generation of a complete patient history. The complete patient history may include personal information such as date of birth, gender, preferred language, a calculated risk score, a payer, an attributed provider, and an appointment schedule. The complete patient history may also include a list of problems and whether the problems were resolved, a list of prescribed medications and filling dates, and vital signs and other clinical information such as weight, height, and blood pressure measurements. The analysis performed to obtain the patient summary displayed in FIG. 8 is made possible by receiving data records from multiple sources and matching records between the sources. For example, the problem list may be assembled from patient diagnosis, the medication list from patient records, and the information regarding when the prescriptions was refilled from billing information.

In one embodiment, analyzing may include grouping the plurality of individuals into separate population cohorts and identifying the population cohorts to which the target individual is grouped, as shown in FIG. 10. Grouping on a patient dashboard may be accomplished by applying filters, such as a provider filter, a reason for contact filter, and/or a status filter. The list of patients matching the applied filters may include data regarding and/or be sorted by patient, provider, reason for contact, status, details, and/or contact priority. In one embodiment, the display may illustrate care coordination measures including CHF admissions, readmissions, COPD admissions, and medication reconciliation.

Figure 14:
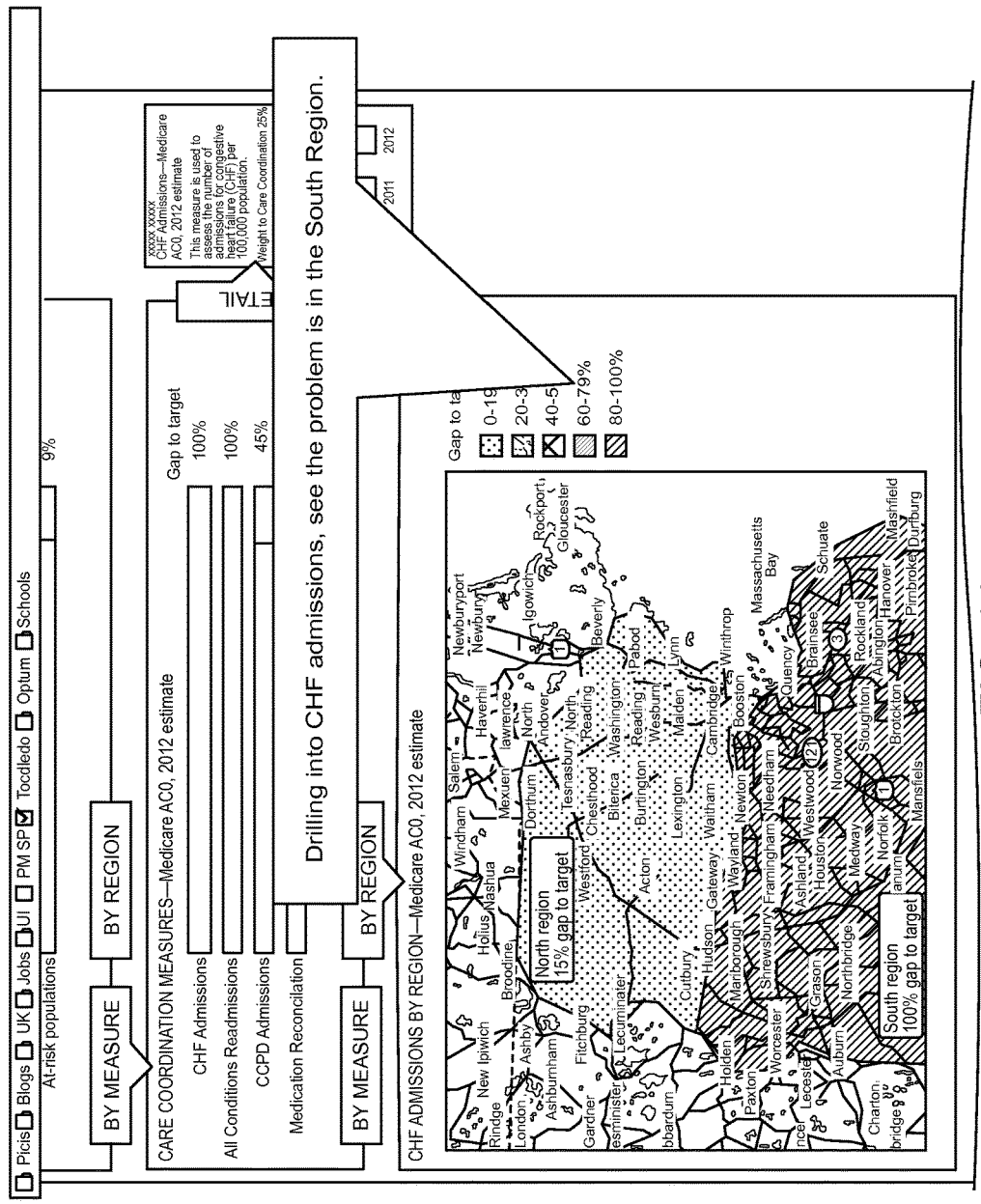
FIG. 14 is an illustration showing a result of displaying multiple data sources on a geographical map according to one embodiment of the disclosure.

In one embodiment, analyzing may include grouping the plurality of individuals into reporting categories such as location. For example, a graphical display, such as a geographical map separated into geographical regions, may illustrate data obtained from multiple sources, as shown in FIG. 14.

Figure 13:
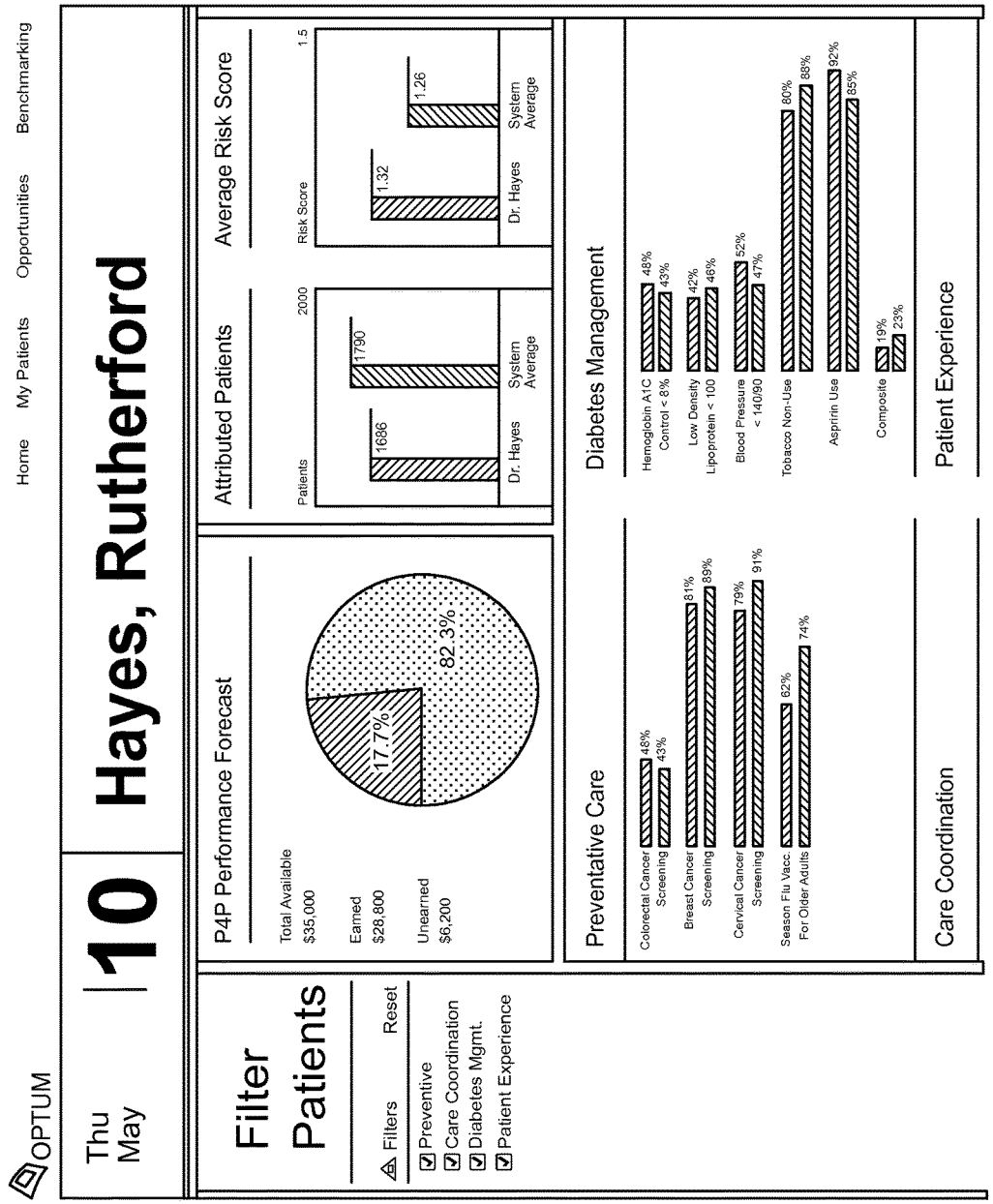
FIG. 13 is an illustration showing a result of analysis to create historical cost and expenditure by clinical category according to one embodiment of the disclosure.

In another embodiment, analyzing may include attributing a clinical condition to the target individual using a predictive model, while in another embodiment, analyzing may include estimating a cost of treatment for the target individual, as shown in FIGS. 9 and 13. For example, an encounter history of FIG. 9 may include recent visits to medical providers, clinical values from those visits, and calculated costs. The information may be compiled, for example, from clinical health care records and billing health care records. The information may also be computed for a particular provider. For example, FIG. 13 illustrates performance of a provider with respect to particular patients. That is, outcomes and costs for treating particular patients by a particular provider may be graphically illustrated, as shown in FIG. 13. The patients for a provider may be filtered by, for example, preventative care, care coordination, diabetes management, and/or patient experience. Results for the provider in treating a group of patients matching the filter may include calculating an average risk score, calculating a P4P performance forecast, and/or calculating outcomes for the patients compared to system averages. For example, the display of FIG. 13 may report the number of the provider's patients matching the filter criteria having a blood pressure greater than 140/90 compared to a system average.

Figure 11:
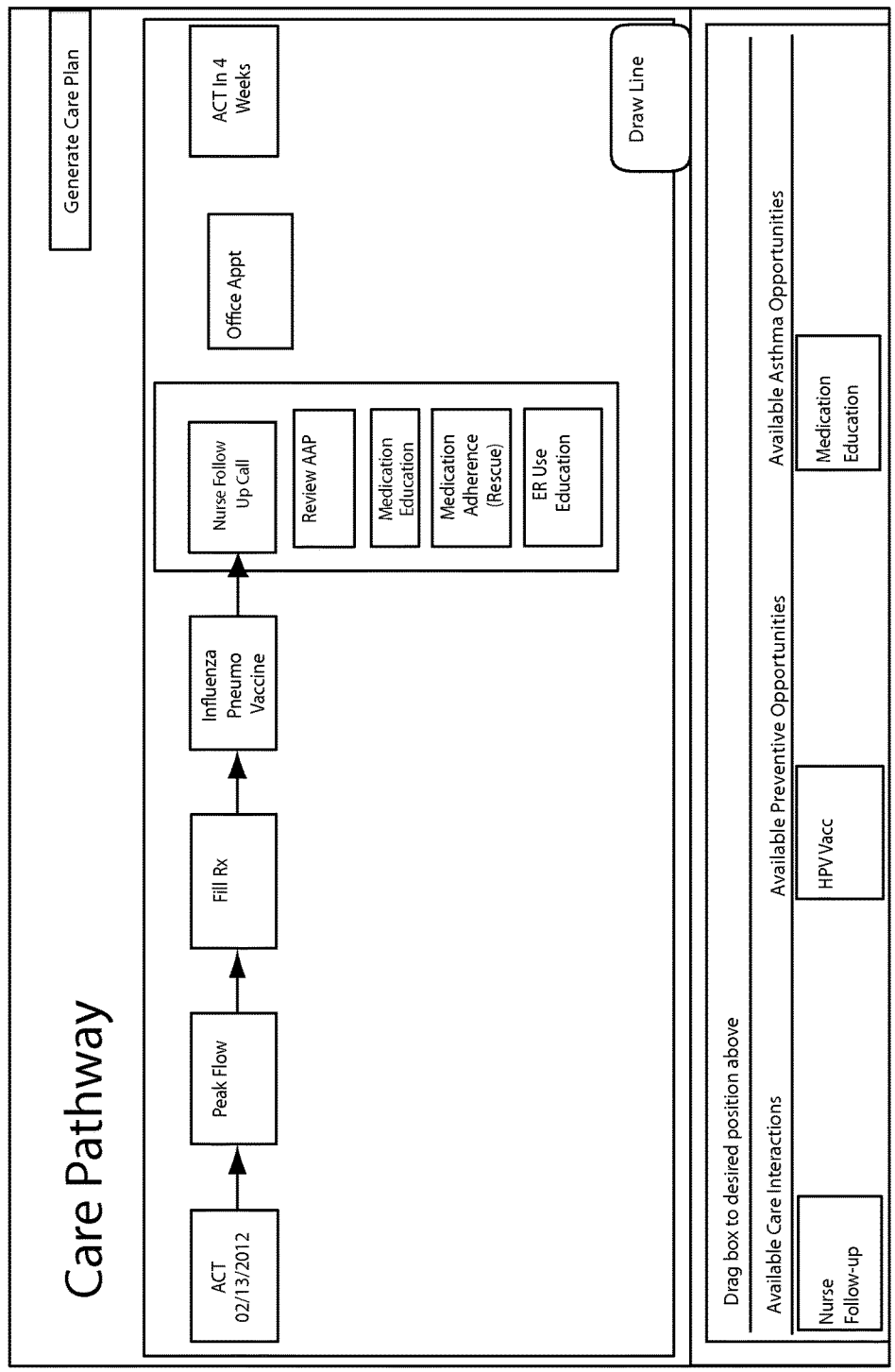
FIG. 11 is an illustration showing a result of an analysis to a care plan according to one embodiment of the disclosure.

In another embodiment, analyzing may include defining a patient care plan for the target individual using the classifications and categories defined by the Pathways application, allowing clinical staff to define new care plans based on historical information, as shown in FIG. 11. A clinical staff member may draw a pathway of care for an individual to include steps of care, such as obtaining prescriptions, obtaining vaccines, receiving educational materials, scheduling follow-up calls, and/or scheduling follow-up appointments. The pathway may be drawn by dragging and dropping available boxes into the flow of the pathway. The display may identify specific opportunities and actions available for a particular patient by analyzing data from multiple sources. For example, when drawing a care pathway for a patient with asthma or a patient at risk for asthma, a "medication education" box may appear in a list of opportunities to add to the care pathway.

According to one embodiment, analyzing may further include identifying a clinical and financial risk associated with the target individual or generating a care plan for the target individual. In yet another embodiment, analyzing may include calculating and displaying a confidence level for a healthcare decision made available to the user of the user interface display, wherein the healthcare decision is associated with the target individual.

Referring back to FIG. 7, the method 700 may further include, at block 710, outputting information to a user interface display based, in part, on the analysis, and identifying a user accessing the user interface display.

All of the methods disclosed and claimed herein can be made and executed without undue experimentation in light of the present disclosure. While the apparatus and methods of this invention have been described in terms of preferred embodiments, it will be apparent to those of skill in the art that variations may be applied to the methods and in the steps or in the sequence of steps of the method described herein without departing from the concept, spirit and scope of the invention. In addition, modifications may be made to the disclosed apparatus, and components may be eliminated or substituted for the components described herein where the same or similar results would be achieved. All such similar substitutes and modifications apparent to those skilled in the art are deemed to be within the spirit, scope, and concept of the invention as defined by the appended claims.

Although the present disclosure and its advantages have been described in detail, it should be understood that various changes, substitutions and alterations can be made herein without departing from the spirit and scope of the disclosure as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the present processes, disclosure, machines, manufacture, compositions of matter, means, methods, or steps, presently existing or later to be developed that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps.

What is claimed is:

1. A secure electronic record information system, comprising:
a secure memory; and
a processor coupled to the secure memory, the processor programmed to:
process a first web service obtaining at least two of a first set of secure data records on a first data storage device data source, a second set of secure data records on a second data storage device data source, a third set of secure data records on a third data storage device data source, and a fourth set of secure data records on a fourth data storage device data source;
match at least one obtained set of secure data records from each obtained set to respective individuals represented in data accessed from a second web service;
group individuals into separate population cohorts as a function of the secure data records for respective individuals;
identify, based on the secure data records, one or more population cohorts to which a target individual is grouped;
attribute, based on the secure data records, classifications to the target individual;
analyze, based on the secure data records, to attribute a clinical condition to the target individual, and to group individuals into reporting categories including location;
determine, by the secure electronic record information system using at least the classifications, at least one parameter comprising a plan parameter for the target individual, a risk parameter of the target individual, and a confidence level parameter for the target individual; and
a graphical user interface outputting the at least one parameter in at least one dashboard display, and
a geographical map display separated into geographical regions illustrating data obtained from the multiple data sources including a geographical distribution of a selected population cohort, where each geographical region indicates a percentage gap to target for a selected care coordination measure.

2. The secure electronic record information system of claim 1 wherein the first set of secure data records is claims healthcare data records, the second set of secure data records is clinical healthcare data records, the third set of secure data records is billing healthcare data records, and the fourth set of secure data records is patient report outcomes healthcare data records.

3. The secure electronic record information system of claim 1 wherein the classifications are clinical classifications.

4. The secure electronic record information system of claim 1 wherein the plan parameter is a care plan for the target individual.

5. The secure electronic record information system of claim 1 wherein the risk parameter is a clinical risk of the target individual.

6. The secure electronic record information system of claim 1 wherein the confidence parameter is a confidence level for a healthcare decision associated with the target individual.

7. The secure electronic record information system of claim 2 wherein the processor is programmed to group individuals into separate population cohorts includes identifying data from the set of clinical healthcare data records relevant to a condition of the target individual.

8. The apparatus of claim 1 wherein the processor identifies a user accessing the user interface and wherein information output to the user interface is unique for the user accessing the user interface.

9. A method of data processing, comprising:
receiving, by a consolidated database, from a first web service of a data processing system server, at least two of a set of first data records on a first data storage device data source, a set of second data records on a second data storage device data source, a set of third data records on a third data storage device data source, and a set of fourth data records on a fourth data storage device data source;
searching, by the data processing system server, the consolidated database comprising the at least two of the set of first data records, the set of second data records, the set of third data records, and the set of fourth data records;
matching, by the data processing system server, at least one received set of data records to respective individuals represented in data accessed from a second web service;
grouping the individuals, by the data processing system server, into separate population cohorts;
identifying, by the data processing system server, one or more population cohorts to which a target individual is grouped;
attributing, by the data processing system server, classifications to the target individual;
analyzing, based on the data records, to attribute a clinical condition to the target individual, and to group individuals into reporting categories including location;
determining, by the data processing system server using at least the classifications, a plan parameter for the target individual;
determining, by the data processing system server, based on the plan parameter, a risk parameter of the target individual;
determining, by the data processing system server, based on the risk parameter, a confidence level parameter for a decision associated with the target individual; and
displaying, by the data processing system server, on a graphical user interface, at least one dashboard display including the determined parameters, and
a geographical map display separated into geographical regions illustrating data obtained from the multiple data sources including a geographical distribution of a selected population cohort, where each geographical region indicates a percentage gap to target for a selected care coordination measure.

10. The method of data processing of claim 9 wherein the set of first data records is claims healthcare data records, the set of second data records a set of clinical healthcare data records, the set of third data records is a set of billing healthcare data records, and the set of fourth data records is a set of patient report outcomes healthcare data records.

11. The method of data processing of claim 9 wherein the searching the consolidated database step comprises searching for at least two of a set of claims healthcare data records, a set of clinical healthcare data records, a set of billing healthcare data records, and a set of patient report outcomes healthcare data records for at least one healthcare data record from each set.

12. The method of data processing of claim 9 wherein the step of grouping the individuals into separate population cohorts includes identifying data from a plurality of sets of healthcare data records relevant to a condition of the target individual.

13. The method of data processing of claim 9 wherein the step of displaying further includes identifying a user accessing the user interface and wherein information output to the user interface is unique for the user accessing the user interface.

* * * * *